United States Patent

Kratz et al.

Patent Number: 5,840,099
Date of Patent: Nov. 24, 1998

[54] PROCESS FOR THE REMOVAL OF WATER, $CO_2$, ETHANE AND $C_3+$ HYDROCARBONS FROM A GAS STREAM

[75] Inventors: Wilbur Clymer Kratz, Macungie; Timothy Christopher Golden, Allentown, both of Pa.; Mohammad Ali Kalbassi, Walton-on-Thames, United Kingdom

[73] Assignee: Air Products and Chemicals, Inc., Allentown, Pa.

[21] Appl. No.: 931,045

[22] Filed: Sep. 16, 1997

[51] Int. Cl.⁶ .................................................. B01D 53/047
[52] U.S. Cl. ................ 95/101; 95/103; 95/105; 95/122; 95/139; 95/143
[58] Field of Search ............... 95/98, 100–105, 95/118, 119, 122, 139, 143, 144

[56] References Cited

U.S. PATENT DOCUMENTS

| | | | |
|---|---|---|---|
| 4,077,779 | 3/1978 | Sircar et al. | 95/101 X |
| 4,493,715 | 1/1985 | Hogan et al. | 95/139 |
| 4,711,645 | 12/1987 | Kumar | 95/122 X |
| 4,784,672 | 11/1988 | Sircar | 95/98 X |
| 4,830,734 | 5/1989 | Nagji et al. | 95/122 X |
| 4,857,083 | 8/1989 | DiMartino | 95/103 X |
| 5,013,334 | 5/1991 | Maurer | 55/26 |
| 5,171,333 | 12/1992 | Maurer | 55/26 |
| 5,174,796 | 12/1992 | Davis et al. | 95/100 |
| 5,186,727 | 2/1993 | Chang | 95/139 X |
| 5,232,474 | 8/1993 | Jain | 95/98 X |
| 5,245,099 | 9/1993 | Mitariten | 95/100 X |
| 5,480,625 | 1/1996 | Nalette et al. | 95/139 X |
| 5,536,300 | 7/1996 | Reinhold, III et al. | 95/101 |
| 5,656,064 | 8/1997 | Golden et al. | 95/104 X |
| 5,656,065 | 8/1997 | Kalbassi et al. | 95/98 X |

FOREIGN PATENT DOCUMENTS

| | | | |
|---|---|---|---|
| 63-107720 | 5/1988 | Japan | 95/122 |

*Primary Examiner*—Robert Spitzer
*Attorney, Agent, or Firm*—Robert J. Wolff

[57] ABSTRACT

A process is set forth for the selective removal of water, $CO_2$, ethane and $C_3+$ hydrocarbons from gas streams, particularly a natural gas stream comprising primarily methane. The process comprises contacting the gas stream with an adsorbent material consisting exclusively of one or more compounds which are basic (i.e. compounds which, when contacted with a pH neutral aqueous solution, cause such solution to have a pH greater than 7.0) and which are mesoporous (i.e. compounds which have moderately small pores providing a surface area less than 500 $m^2/g$). The key to the present invention is the use of a single homogenous adsorbent without sacrificing performance. Typical mesoporous adsorbents which are useful in the present invention include zinc oxide, magnesium oxide and, in particular, activated alumina.

9 Claims, No Drawings

PROCESS FOR THE REMOVAL OF WATER, $CO_2$, ETHANE AND $C_3+$ HYDROCARBONS FROM A GAS STREAM

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

Pipeline natural gas is commonly liquefied for storage to smooth the peaks in demand between winter and summer. Water and $CO_2$ removal is required in this application to prevent freeze out during the low temperature liquefaction step. More recently, a market has developed for methane as a transportation fuel. Again, the pipeline nature gas is liquefied for storage, but in this case $C_3+$ hydrocarbons must be removed in addition to the water and $CO_2$ to maintain a uniform fuel composition. Water and $CO_2$ are typically removed by Thermal Swing Adsorption (TSA) while some form of cryogenic distillation is used for the $C_3+$ separation. This is a relatively complex operation. As the level of $CO_2$ in the pipeline increases to between 1.5 and 2%, conventional TSA systems become capacity limited and therefore run on short cycle times. The short cycle times increase the amount of regeneration gas (produce methane) required which lowers the product methane recovery to the low 80's%. For higher $CO_2$ levels, the conventional technology would be chemical absorption followed by a drier. Absorption systems are undesirable because of operational and maintenance problems and the resulting combination of absorption, drying and cryogenic distillation is both complicated and expensive. A one step process that simultaneously removes water, $CO_2$ and $C_3+$ hydrocarbons would be much simpler and cost effective but such a process is not available at this time. The process of the present invention addresses this need. The process comprises contacting the gas stream with an adsorbent material consisting exclusively of one or more compounds which are basic (i.e. compounds which, when contacted with a pH neutral aqueous solution, cause such solution to have a pH greater than 7.0) and which are mesoporous (i.e. compounds which have moderately small pores providing a surface area less than 500 $m^2/g$). Typical basic, mesoporous adsorbents which are useful in the present invention include zinc oxide, magnesium oxide and, in particular, activated alumina.

The closest prior art to the present invention is represented by U.S. Pat. Nos. 5,013,334 and 5,171,333, both by Maurer and assigned to UOP (hereafter "Maurer"). Maurer teaches microporous adsorbents consisting of the zeolitic molecular sieves ZnX and CaY for separating ethane from methane-containing feed streams. These adsorbents were shown to be more effective for ethane removal than the traditionally used 13X zeolite. Maurer also teaches that it may be desirable to employ an additional adsorbent such as silica gel, activated carbon, or activated alumina where the removal of water and $C_3+$ hydrocarbons is also required. Maurer also discusses the problem of methane coadsorption in his separation. Methane coadsorption occurs because microporous adsorbents like the zeolites and carbons taught in Maurer coadsorb significant quantities of methane owing to the high inlet partial pressure of methane which in turn causes thermal problems during processing in a pressure swing adsorption (PSA) system. In particular, methane coadsorption causes heating during the adsorption step and cooling during the desorption step. This thermal behavior runs counter to what is desired in PSA systems since the equilibrium loading of many adsorbates such as ethane is reduced at higher temperatures.

The present invention has found that, in addition to providing for water and $C_3+$ removal, basic adsorbents such as activated alumina can also provide for $CO_2$ removal down to low (less than 50 ppm) levels where the $CO_2$ is present in dilute (1–5%) concentrations. This is due to the interaction of basic sites on the activated alumina with the acidic $CO_2$ molecule. In addition, the present invention has also found that activated alumina can provide for ethane removal down to modest (1–2%) levels where the ethane is present in dilute (1–10%) concentrations. Thus, the selective removal of water, $CO_2$, ethane and $C_3+$ hydrocarbons from gas streams such as methane is possible with a single adsorbent without sacrificing performance.

Furthermore, the mesoporous nature of adsorbents such as activated alumina also provides other key advantages vis-a-vis microporous adsorbents like the zeolites and carbons taught in Maurer. In general, as the pore size of an adsorbent increases, adsorption capacity for non-polar adsorbates such as methane and $C_3+$ hydrocarbons decreases. Hence, methane and $C_3+$ hydrocarbons are more weakly adsorbed on activated alumina vis-a-vis microporous adsorbents. This provides for a reduction in the thermal problems associated with the coadsorption of methane as noted above. This also provides for easier desorption of the $C_3+$ hydrocarbons when regenerating the adsorbent while still providing for sufficient adsorption of dilute $C_3+$ hydrocarbons during the adsorption step. (Although activated alumina's affinity for $C_3+$ hydrocarbons is less than the affinity of Maurer's microporous adsorbents for $C_3+$ hydrocarbons, activated alumina's affinity is nonetheless a more optimum affinity where the $C_3+$ hydrocarbons are present in dilute (1–2%) concentration and where the adsorbent must be continually regenerated).

BRIEF SUMMARY OF THE INVENTION

The present invention is a process for the selective removal of water, $CO_2$, ethane and $C_3+$ hydrocarbons from gas streams, particularly a natural gas stream comprising primarily methane. The process comprises contacting the gas stream with an adsorbent material consisting exclusively of one or more compounds which are basic (i.e. compounds which, when contacted with a pH neutral aqueous solution, cause such solution to have a pH greater than 7.0) and which are mesoporous (i.e. compounds which have moderately small pores providing a surface area less than 500 $m^2/g$). The key to the present invention is the use of a single homogenous adsorbent without sacrificing performance. Typical basic, mesoporous adsorbents which are useful in the present invention include zinc oxide, magnesium oxide and, in particular, activated alumina.

BRIEF DESCRIPTION OF THE SEVERAL VIEWS OF THE DRAWINGS

Not applicable.

DETAILED DESCRIPTION OF THE INVENTION

The present invention is a process for the selective removal of water, $CO_2$, ethane and C3+ hydrocarbons from gas streams, particularly natural gas streams comprising primarily methane. The process comprises contacting the gas stream with an adsorbent material consisting exclusively of one or more compounds which are basic (i.e. compounds which, when contacted with a pH neutral aqueous solution, cause such solution to have a pH greater than 7.0) and which are mesoporous (i.e. compounds which have moderately small pores providing a surface area less than 500 m$^2$/g). In contrast to microporous compounds which have very small pores and thus provide very large surface areas for the mechanism of adsoprtion to take place on, mesoporous compounds have only moderately small pores and thus provide only moderately large surface areas. Typical basic, mesoporous adsorbents which are useful in the present invention include zinc oxide, magnesium oxide and, in particular, activated alumina.

The skilled practitioner will appreciate that the pH limitation of the present invention would commonly be referred to in the art as the adsorbent having a "zero point of charge" greater than 7.0 The skilled practitioner will further appreciate that the surface area limitation of the present invention can be measured by the BET method which is based on the multilayer adsorption theory developed in 1938 by Brunauer, Emmett and Teller.

The process of the present invention is particularly designed to treat a typical natural gas feed stream which is at high pressure (about 500 psig for natural gas pipelines), saturated with water (about 700 ppm for a gas stream at ambient temperature and 500 psig) and further contains about 1–3% $CO_2$, about 1–10% ethane and about 1–2% $C_3$+ hydrocarbons with the remaining 85–97% being methane. The process of the present invention is designed to simultaneously remove water, $CO_2$, some ethane and all $C_3$+ hydrocarbons from this feed stream in order to produce a purified stream containing about 98–99% methane, about 1–2% ethane and less than about 50 ppm $CO_2$ wherein about 90% of the methane in the feed gas stream is recovered in the purified stream.

Preferably, the step of contacting of the natural gas stream with the adsorbent is performed within a pressure swing adsorption (PSA) vessel containing said adsorbent and is followed by an adsorbent regeneration sequence comprising the steps of depressurizing/venting the adsorption vessel down to low pressure followed by repressurizing the adsorbent-containing vessel with a portion of the purified gas stream back to the pressure level at which the gas stream was initially contacted with the adsorbent.

Also preferably, the depressurization is partly performed via one or more pressure equalization steps with other PSA vessels undergoing said repressurizing. The skilled practitioner will appreciate that this will recover some of the void methane and thus improve the recovery of the methane, albeit at the expense of additional PSA vessels operating sequentially in parallel with one another.

Also preferably, the depressurizing is performed down to vacuum pressure levels by connecting the adsorption vessel to a vacuum pump (i.e. vacuum swing adsorption or VSA). The skilled practitioner will appreciate that this will improve the adsorbent's rejection of the adsorbed impurities during the depressurization step, albeit at the expense of power.

Also preferably, the adsorbent is purged or rinsed with a portion of the purified gas stream subsequent to said depressurization step and prior to said repressurization step. The skilled practitioner will appreciate that this will further improve the adsorbent's rejection of the adsorbed impurities, albeit at the expense of methane recovery. Note however that in a typical PSA process, the purge step is performed at 1 atm pressure. By lowering the purge pressure to 0.1 atm, one can obtain the same degree of purging with about 10% of the gas required at 1 atm Thus the methane recovery penalty associated with purging is much less severe in a VSA process as opposed to a PSA process.

Also preferably, the steps of the process are performed as a continually repeating cycle of steps in a system comprising a plurality of adsorption vessels which each undergo their respective cycle of steps while collectively operated sequentially in parallel with one another. The cycle time depends on the specific design but typically might be one minute per step.

EXAMPLE 1

A natural gas feed composition of 0.5% $N_2$, 1.3% $CO_2$, 94.7% methane, 2.2% ethane, 1% C3, 0.11% C4, 0.05% C5, 0.02% C6, 0.02% C7 and 0.003% C8 was processed in the above described preferred embodiment of the present invention. The adsorbent was activated alumina (Alcan AA-300 made by The Aluminum Company of Canada) having a BET surface area equal to 325 m$^2$/g. Three pressure equalization steps and six adsorption vessels were utilized. The final evacuation and purge pressure was 1.5 psia. The process was run for over 10,000 cycles to demonstrate that the $C_3$+ hydrocarbons were not accumulating in the adsorbent and degrading the performance. The product methane composition was 0.5% $N_2$, 0.0029% $CO_2$, 98.3% methane and 1.2% ethane. The methane recovery was 90%. This example demonstrates the use of a single adsorbent in a methane purification process while still achieving performance objectives including (i) less than 50 ppm C02, (ii) no $C_3$+ hydrocarbons, (iii) less than 2% ethane and (iv) high methane recovery. Conventional wisdom for the separation in this example might have suggested a bed of activated carbon followed by 13X molecular sieve for this application. This adsorbent arrangement is suggested by Maurer in U.S. Pat. No. 5,013,334 and is the catalyst arrangement in Example 2 below.

EXAMPLE 2

The operating conditions are roughly the same as in Example 1 except the adsorbent arrangement is a 38–62% carbon-13X split. The result was a rapid decline in performance. Even with fresh adsorbent, there was difficulty holding the product $CO_2$ level to 50 ppm and after only a few cycles (about 20 to 30) the performance had degraded significantly. In particular, the $CO_2$ level increased to 130 ppm and the evacuation gas per cycle declined by about 25%. Similar results were seen with an all 13X bed. The BET surface area of the activated carbon was 1000 m$^2$/g and that for the 1 3X was 825 m$^2$/g. The key negative results noted here are (i) zeolites, despite high $CO_2$ capacity and selectivity, could not produce a low impurity level $CO_2$ product and (ii) activated carbon, often used for hydrocarbon removal, was ineffective in "self-cleaning" heavy hydrocarbons from the feed stream under VSA operating conditions as noted by degrading process performance over time. Contrast these results with the activated alumina used in Example 1 which unexpectedly provided a good combination of good working $CO_2$ capacity, high purity $CH_4$ product (low $CO_2$ impurity) and the ability to reject heavy hydrocarbons at the operating conditions of the process.

We claim:

1. A process for the selective removal of water, $CO_2$, ethane and $C_3$+ hydrocarbons from a gas stream in order to produce a purified gas stream, said process comprising the step of contacting the gas stream at elevated pressure with an adsorbent material consisting exclusively of one or more compounds which are basic (i.e. compounds which, when contacted with a pH neutral aqueous solution, cause such solution to have a pH greater than 7.0) and which are mesoporous (i.e. compounds which have moderately small pores providing a surface area less than 500 m$^2$/g).

2. The process of claim 1 wherein the adsorbent is one or more compounds selected from the group consisting of activated alumina, zinc oxide and magnesium oxide.

3. The process of claim 2 wherein the gas stream is a natural gas stream comprising primarily methane.

4. The process of claim 3 wherein the natural gas stream is at an elevated pressure of about 500 psig pressure and contains about 700 ppm water, about 1–3% $CO_2$, about 1–10% ethane and about 1–2% $C_3$+ hydrocarbons and about 85–97% methane.

5. The process of claim 4 wherein the purified gas stream contains about 98–99% methane, about 1–2% ethane and less than about 50 ppm $CO_2$ and wherein about 90% of the methane in the natural gas stream is recovered in the purified gas stream.

6. The process of claim 5 wherein said contacting of the gas stream at elevated pressure with the adsorbent is performed within a pressure swing adsorption (PSA) vessel containing said adsorbent.

7. The process of claim 6 wherein following the step of contacting the gas stream at elevated pressure with the adsorbent, said process further comprises an adsorbent regeneration sequence comprising a depressurization step comprising depressurizing the adsorption vessel down to low pressure followed by a repressurization step comprising repressurizing the adsorbent-containing vessel with a portion of the purified gas stream back to the pressure level at which the gas stream was initially contacted with the adsorbent.

8. The process of claim 7 wherein:
   (i) said depressurization step is partly performed via one or more pressure equalization steps with other PSA vessels undergoing said repressurization step;
   (ii) said depressurization step is performed down to vacuum pressure levels; and
   (iii) the adsorbent is purged with a portion of the purified gas stream subsequent to said depressurization step and prior to said repressurization step.

9. The process of claim 8 wherein the steps of the process are performed as a continually repeating cycle of steps in a system comprising a plurality of adsorption vessels which each undergo their respective cycle of steps while collectively operated sequentially in parallel with one another.

* * * * *